United States Patent [19]

Hochberg et al.

[11] Patent Number: 5,071,251
[45] Date of Patent: Dec. 10, 1991

[54] WAVELENGTH INDEPENDENT INTERFEROMETER

[75] Inventors: Eric B. Hochberg, Altadena; Norman A. Page, Monrovia, both of Calif.

[73] Assignee: California Institute of Technology, Pasadena, Calif.

[21] Appl. No.: 364,165

[22] Filed: Jun. 12, 1989

[51] Int. Cl.$^5$ .............................................. G01B 9/02
[52] U.S. Cl. ..................................... 356/359; 356/360
[58] Field of Search ............... 356/346, 349, 359, 360; 351/212

[56] References Cited

U.S. PATENT DOCUMENTS

| | | | |
|---|---|---|---|
| 4,810,093 | 3/1989 | Doyle | 356/346 |
| 4,832,489 | 5/1989 | Wyant et al. | 356/359 |

Primary Examiner—Davis L. Willis
Assistant Examiner—Matthew W. Koren
Attorney, Agent, or Firm—Leonard Tachner

[57] ABSTRACT

A polychromatic interferometer utilizing a plurality of parabolic reflective surfaces to properly preserve the fidelity of light wavefronts irrespective of their wavelengths as they pass through the instrument is disclosed. A preferred embodiment of the invention utilizes an optical train which comprises three off-axis parabolas arranged in conjunction with a beam-splitter and a reference mirror to form a Twyman-Green interferometer. An illumination subsystem is provided and comprises a pair of lasers at different preselected wavelengths in the visible spectrum. The output light of the two lasers is coaxially combined by means of a plurality of reflectors and a grating beam combiner to form a single light source at the focal point of the first parabolic reflection surface which acts as a beam collimator for the rest of the optical train. By using visible light having two distinct wavelengths, the present invention provides a long equivalent wavelength interferogram which operates at visible light wherein the effective wavelength is equal to the product of the wavelengths of the two laser sources divided by their difference in wavelength. As a result, the invention provides the advantages of what amounts to long wavelength interferometry but without incurring the disadvantage of the negligible reflection coefficient of the human eye to long wavelength frequencies which would otherwise defeat any attempt to form an interferogram at that low frequency using only one light source.

10 Claims, 4 Drawing Sheets

WAVELENGTH INDEPENDENT INTERFEROMETER

ORIGIN OF INVENTION

The invention described herein was made in the performance of work under NASA contract No. NAS-7-918, and is subject to the provisions of Public Law 96-517 (35 USC 202) in which the Contractor has elected to retain title.

TECHNICAL FIELD

The present invention relates generally to interferometric optics and more specifically to an optical system for use in making interferometric measurements and that is especially advantageous for making such measurements for topographical mapping of aspherical surfaces. Because of the unique properties of the present invention, it is especially useful for topographically mapping the shape of the human cornea by developing visibility fringes from two simultaneously present interference patterns by using light of two different wavelength patterns.

BACKGROUND ART

Corneal surgery is currently undergoing rapid evolution with improvements designed to minimize or eliminate astigmatism following penetrating keraplasty (corneal transplants), as well as to correct refractive error. Because the cornea is the most powerful refracting surface of the eye, numerous procedures have been devised to incise, lathe, freeze, burn and reset the cornea to alter its shape. Currently practiced keratorefractive surgical techniques include: cryorefractive techniques (keratomileusis, keratophakia, ipikeratophakia), radialkeratotomy, thermal keratoplasty, corneal relaxing incisions and wedge resections.

When preparing the patient for any of these surgical techniques, it is essential to accurately measure the corneal curvature. Existing methods to measure corneal curvature include central keratometry and photokeratoscopy with central keratometry. However, with these methods the diameter of the cornea that can be accurately measured is limited. Recently, photokeratoscopy has been adapted to provide a topographic map of the cornea. However, existing keratometers are limited in two important regards. Firstly, these instruments are predicated on geometrical image forming principles and assume the corneal topography can be expressed in terms of zones of various spherical radii. This in turn involves assumptions as to the nature of the surface under test. With more strongly aspheric corneas or as larger areas on even the average or typical size cornea are considered, the measurement becomes extremely ambiguous. Secondly, primarily as a consequence of the above but also because of optical engineering considerations, most instruments are limited in terms of the aperture of the cornea that can be measured. Existing instruments typically cover corneal diameters no greater than three millimeters. An additional problem one must consider in the design of a clinically useful instrument is the relatively low corneal specular reflectivity which is approximately two percent in the visible light range and virtually zero in the infrared light range.

While it is recognized that optical interferometric techniques for non-invasive measurement of corneal topography provide the only way of producing a contour map of the corneal surface directly, it is also recognized that visible light interferograms (operating wavelengths less than 0.7 microns) would typically result in the requirement to contend with hundreds of densely packed fringes even when the cornea under test is compared to an optimally fitting reference sphere. This problem is a consequence of the strongly aspheric nature of the typical cornea. Such interferograms require commensurately high resolution detection well beyond for example, the range of currently available detector arrays. Furthermore, such high submicron topographic sensitivity resulting from the use of such short wavelength light is unnecessary. If the reflectivity of the surface of the eye were not negligible in the infrared range (10–50 microns), a standard interferometric test performed using a single infrared wavelength would be an ideal solution, because no new technology would be required. Unfortunately, this is not the case. Thus there is still an ongoing need for a real-time keratometer system for medical diagnosis and for preparation of a corneal contour for eye surgery, as well as, for post-operative analysis of completed eye surgery.

STATEMENT OF INVENTION

The present invention solves the aforementioned need by providing a visible light alternative to infrared interferometry, but which still provides long equivalent-wavelength results thereby overcoming the densely-packed fringe problem of the prior art. This solution is the use of a two-wavelength interferometric technique where visible light of two different wavelengths is coaxially reflected onto the corneal surface to result in a long equivalent wavelength interferogram. This solution is made possible in the present invention by the use of a novel multi-wavelength interferometer utilizing a plurality of off-axis parabolic reflective surfaces to properly preserve the fidelity of the two wavefronts as they are reflected off the cornea and pass through the instrument. One problem associated with a two-wavelength interferometer is the need to properly achromatize the optical train in the interferometer. Achromatization in this application refers to preservation of the fidelity of the two wavefronts as they pass twice through the optical system of the instrument. Preservation of the fidelity of the wavefronts may be expressed in terms of the amount of optical path difference that is gained or lost as the test surface wavefronts pass through and are combined by the system.

A preferred embodiment of the present invention utilizes an optical train which comprises three off-axis parabolas. The first such parabola acts as a collimator. The second forms a spherical wavefront converging on the cornea and, following the second reflection, preserves the optical path differences of the aberrated wavefront. The third parabola forms an image of the cornea on the detector. These three parabolic reflecting surfaces are arranged in conjunction with a beam splitter and a reference mirror to form a Twyman-Green type interferometer.

The illumination subsystem of the present invention comprises a pair of lasers at different preselected wavelengths in the visible spectrum. The output light of the two lasers is coaxially combined by means of a plurality of reflectors and a grating beam combiner to form a single light source at the focal point of the first parabolic reflection surface which acts as a beam collimator for the rest of the optical train. The third parabolic reflecting surface focuses all of the optical wavefronts necessary to produce the two interferograms onto an interferogram imaging lens which is selected to transmit the collected light onto a detector such as a CCD detector array. The third parabla forms an image of the cornea on the detector. Consequently, the fringe pattern seen on the detector is indicative of the OPD between the cornea-reflected wavefront and the reference spherical wavefront incident on the cornea. Collimated light transmitted by the beam splitter passes onto the second parabolic reflector which forms a converging, spherical "test" wavefront. (Nominally, the cornea retroreflects this wavefront, and nominally, after being reflected by the parabola adjacent the cornea, the wavefront is recollimated). Collimated light reflected by the beam splitter passes to a plano mirror which forms a flat "reference" wavefront which, after being transmitted by the beam splitter, interferes with the cornea/test wavefront. The detector is used to extract the necessary data from the interferograms to define the contour of the aspheric surface which in this case is a human cornea.

It will be seen hereinafter that by using visible light having two distinct wavelengths, the present invention provides a long equivalent wavelength interferogram. The effective wavelength is equal to the product of the wavelengths of the two laser sources divided by the difference in the wavelengths of those sources. This corresponds to an effective frequency which is equal to the difference in the frequency of the two laser sources. Consequently, the apparent or effective frequency of the combined laser light may be selected to be significantly lower than the actual frequency of the visible light of each such laser. As a result, the present invention provides the advantages of what amounts to long wavelength interferometery but without incurring the disadvantages of the negligible reflectivity of the human eye to long wavelengths.

While the particular embodiment of the invention disclosed herein is shown for use in measuring the contour of the cornea of the human eye, it will be understood that the unique fidelity preservation characteristics of the optical train of the invention, permits interferometry applications for the measurement of any aspheric surface and at virtually any wavelength. Thus for example, the present invention will also be useful in the measurement of aspheric surface characteristics at different light wavelengths without requiring any alteration in the optical train which would otherwise be required in prior art optical trains which are typically designed for monochromatic operation.

OBJECTS OF THE INVENTION

It is therefore a principal object of the present invention to provide an optical train for interferometric measurements at any and all wavelengths.

It is an additional object of the present invention to provide a wavelength independent optical system for use in an interferometer.

It is still an additional object of the present invention to provide an optical interferometer which preserves the fidelity of the optical wavefronts of at least two different wavelengths of light for enabling the topographic measurement or contour mapping of highly aspheric reflective surfaces.

It is still an additional object of the present invention to provide an improved keratometer for mapping the contour of the human cornea by using simultaneously two different wavelengths of coaxially aligned light reflected onto the cornea for generating two interferograms, the combined beat fringes of which constitute a long equivalent wavelength interferogram for defining the contour of the cornea being measured.

BRIEF DESCRIPTION OF THE DRAWINGS

The aforementioned advantages and objects of the present invention, as well as additional objects and advantages thereof will be more fully understood hereinafter as a result of a detailed description of a preferred embodiment when taken in conjunction with the following drawings in which.

DETAILED DESCRIPTION OF THE INVENTION

Figure 1:
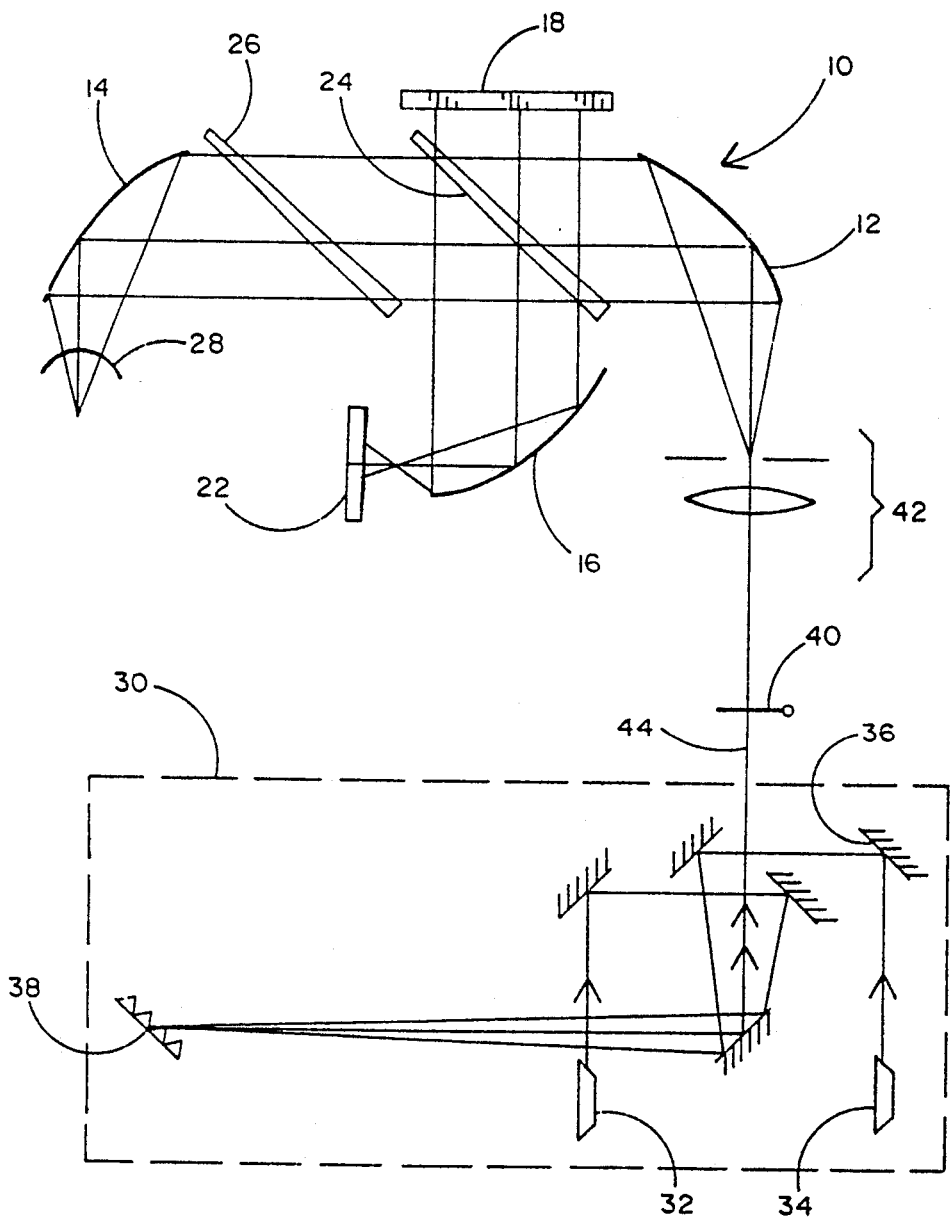
FIG. 1 is a schematic representation of the preferred embodiment of the present invention when used as a keratometer for mapping the contour of the human cornea.
Figure 2:
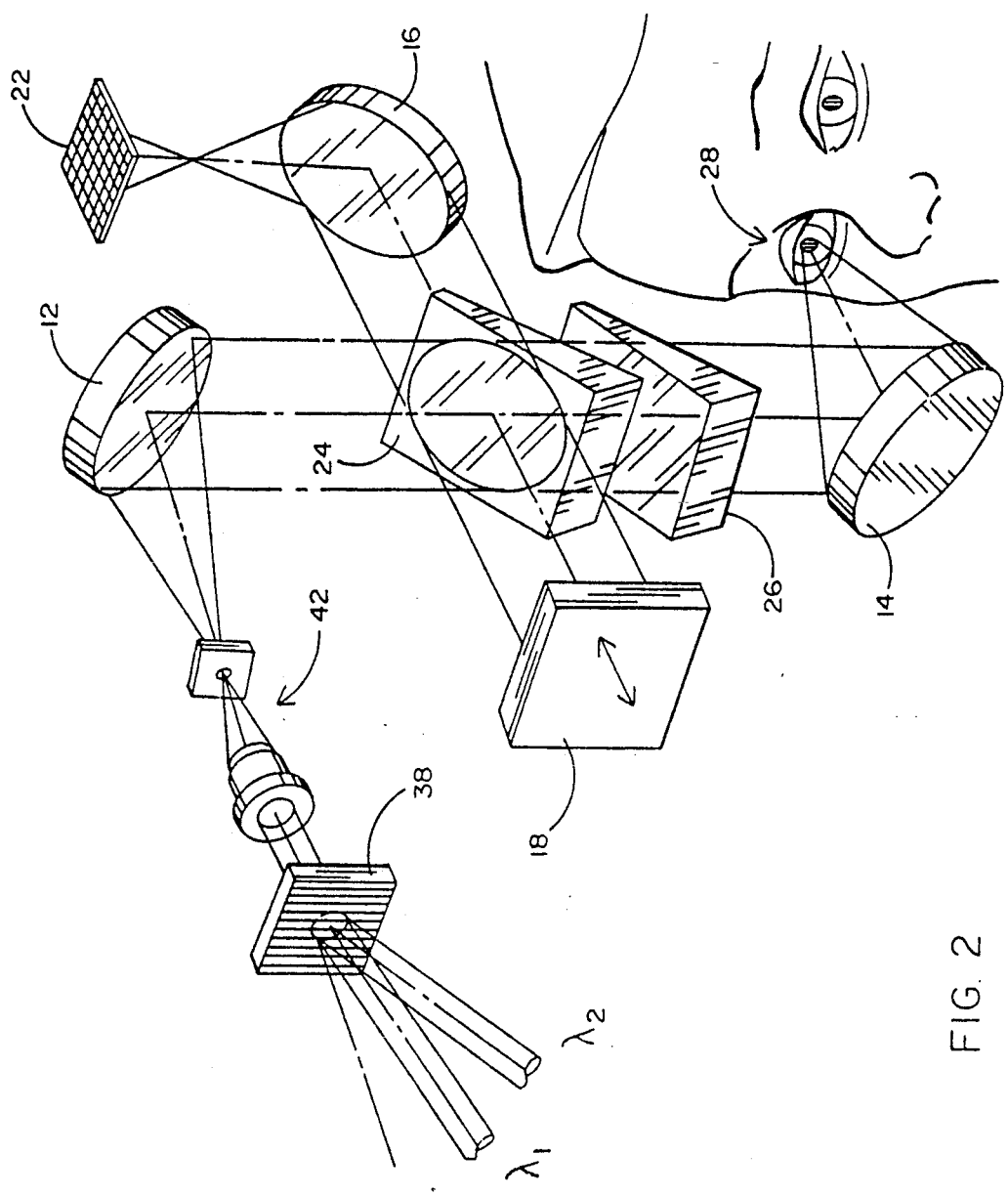
FIG. 2 is a representation of the physical components and their relative positions for generating a long equivalent wavelength interferogram using the present invention.

Referring now to FIGS. 1 and 2, it will be seen that the multi-wavelength interferometer 10 of the present invention comprises a parabolic beam collimator surface 12, a parabolic focusing surface 14, a parabolic imaging surface 16, a reference reflecting mirror 18, a detector 22, a beam splitter 24 and a compensator 26. The interferometer 10 may allow the measurement of aspheric surfaces with a light source of arbitrary wavelength(s). However, as previously noted, when the optical train of the interferometer 10 of the present invention is used for measuring or mapping the contour of a cornea 28, the light source is advantageously a coaxial superposition of two different monochromatic wavelengths of light which may for example be generated in the manner described in FIG. 1.

More specifically, a suitable illumination subsystem 30 for use in the present invention comprises a first laser 32, a second laser 34, a plurality of reflectors 36, a reflective linear diffraction grating 38 for making the beam coaxial, a shutter 40 and a microscope objective beam expander and spatial filter 42. Circularly variable neutral density filters may be used in the light path of one or both of the lasers 32 and 34 to provide additional means for controlling the intensity of light which ultimately reaches the cornea 28.

The purpose of the illumination subsystem 30 shown in FIG. 1 is to provide what may be considered a point source of light having two distinctive monochromatic wavelengths and being positioned at the focal point of parabolic beam collimator surface 12. This is accomplished by directing the output of the respective lasers 32 and 34 by means of reflectors 36 onto a reflective linear diffraction grating beam combiner 38 resulting in the production of a unitary beam 44 which is controlled by a shutter 40 and properly shaped and positioned by means of a microscope objective beam expander and spatial filter 42 at the focal point of parabolic beam collimator surface 12.

The function of collimator 12 is to provide a collimated wavefront which travels from right to left as seen in FIG. 1. A selected fraction of this collimated wavefront of light is passed through a beam splitter 24 which is preferably of a wedged coated glass configuration which provides an optimum equivalent single surface beam splitter characteristic. The light passing through the beam splitter to the left in FIG. 1 impinges upon parabolic focusing surface 14 which focuses the reflected light to a point beyond the cornea or other aspheric surface to be measured. The light reflected from the cornea or other such aspheric surface, retraces the path of the incident light in the reverse direction up to the beam splitter 24 where it is reflected downwardly in FIG. 1 onto the parabolic imaging surface 16.

That portion of the collimated light traveling from right to left as shown in FIG. 1 which is not transmitted by the beam splitter, but is instead reflected thereby, impinges upon a reference mirror 18 which is positioned and oriented properly to provide a plano reference wavefront which will be made to interfere with the light reflected from the cornea 28. Compensator 26 comprises a beam splitter compensator plate which is identical in shape to beam splitter 24, but which is transparent and thus provides path length compensation so that the light traveling to and from the cornea 28 will pass through the same thickness of the same material as the light reflected to the mirror 18 which is in turn reflected back through the beam splitter 24.

The focal length and F-number of the parabolic reflecting surfaces 14 and 16 should be the same and should be selected to provide focal lengths commensurate with the size and general shape of the aspheric surface to be mapped. In the case of a human cornea, it has been found desirable to use an F-number equal to 1.0 for each of the parabolic reflecting surfaces. In most applications for aspherical surface measurement for which the present invention may be used, the F number of the parabolic reflecting surfaces 14 and 16 is contemplated to be within the range of 0.6 and 20.0. The F-number of surface 12 does not necessarily have to be equal to the F-number of the other two parabolic surfaces, but is, for practical size and scaling purposes, likely to be in the same range.

When the multi-wavelength interferometer of the present invention is used with a illumination subsystem 30 of the type shown in FIG. 1, the superposition of two independent interferograms (one for each monochromatic source wavelength) will contain a periodic variation in fringe contrast, visibility or modulation. Whereas the contrast of either of the two fundamental interferograms alone would be uniformly high over the entire aperture, when both interference patterns are present simultaneously, the fringe contrast will be observed to periodically diminish to zero (i.e. the net irradiance will equal the average irradiance level). These "visibility fringes" or "beat fringes" may be thought of as a third interferometric representation of the surface under test, where the effective wavelength or contour interval is given by:

$$\lambda_{effective} = \lambda_1 \lambda_2 / (\lambda_1 - \lambda_2)$$

For example, when the 0.633 micrometer "red" helium-neon laser line is combined with a 0.613 micrometer "orange" line from another helium-neon laser, the effective wavelength is an infrared-like 19.4 micrometers. Thus the visibility fringes occur with a contour interval approximately 30 time coarser than either of the two fundamental fringe frequencies. Because of the reflective (double pass) nature of the measurement, each successive visibility fringe corresponds to a 19.4/2 = 9.7 micron difference in optical path between the actual surface and the reference sphere. For clinical use, the optical path difference (OPD) information can easily be converted to surface height relative to a flat reference surface. The fringe pattern observed at the exit pupil of the interferometer contains both fundamental interferograms and the "beat" interferogram of interest.

The following data in TABLES 1 and 2 demonstrate the preservation of OPD in the keratometer optical system of the present invention. The two sets of data represent the OPD values at two different places in the keratometer optical system. The first set of TABLE 1 gives the OPD values between the elliptical cornea reflecting surface and a reference sphere with the same vertex radius of curvature. The second set of data of TABLE 2 gives the OPD values for the entire optical system at the detector. In a perfect system, the two sets of data would be identical. Six rays were traced in each case and evaluated. The ray number is given in the first column. The height of the ray on the corneal surface is given in the second column. The optical path length for the ray in the part of the optical system analyzed is given in the third column. The last column gives the difference in optical path length between the first ray and the other rays. The first ray is coincident with the axis of the optical system.

The OPD values in each set of data represent precisely the differences between the reference sphere and the cornea. The resulting interference fringe pattern on the detector is digitized and reduced to very accurate cornea surface topography.

Figure 3:
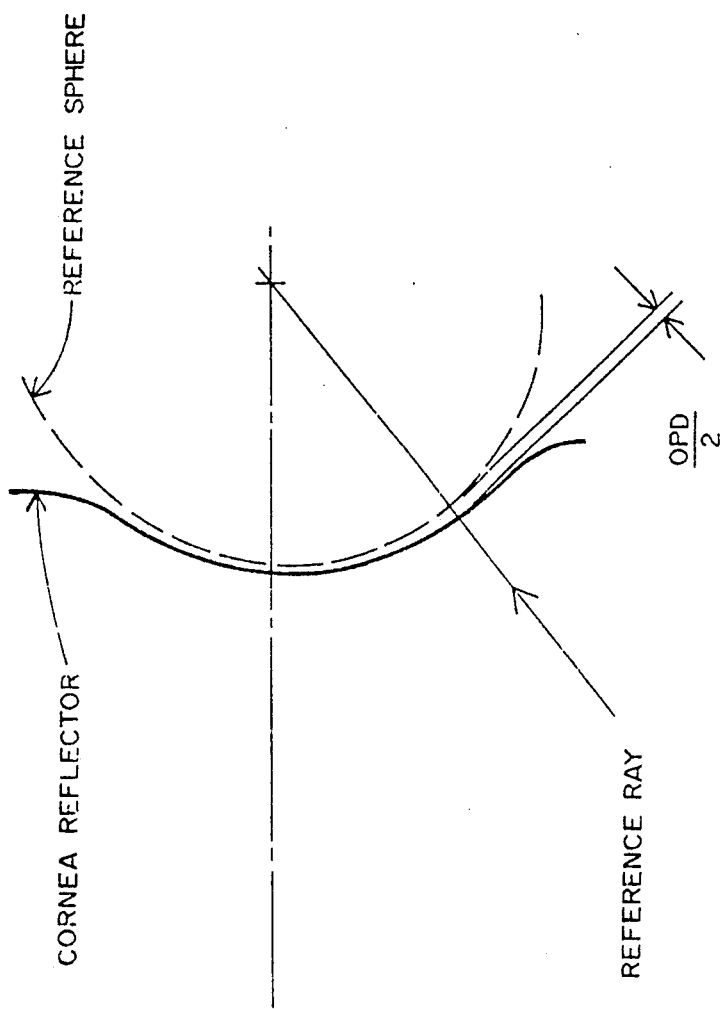
FIG. 3 is a schematic illustration of optical path differences between the cornea and a reference sphere.
Figure 4:
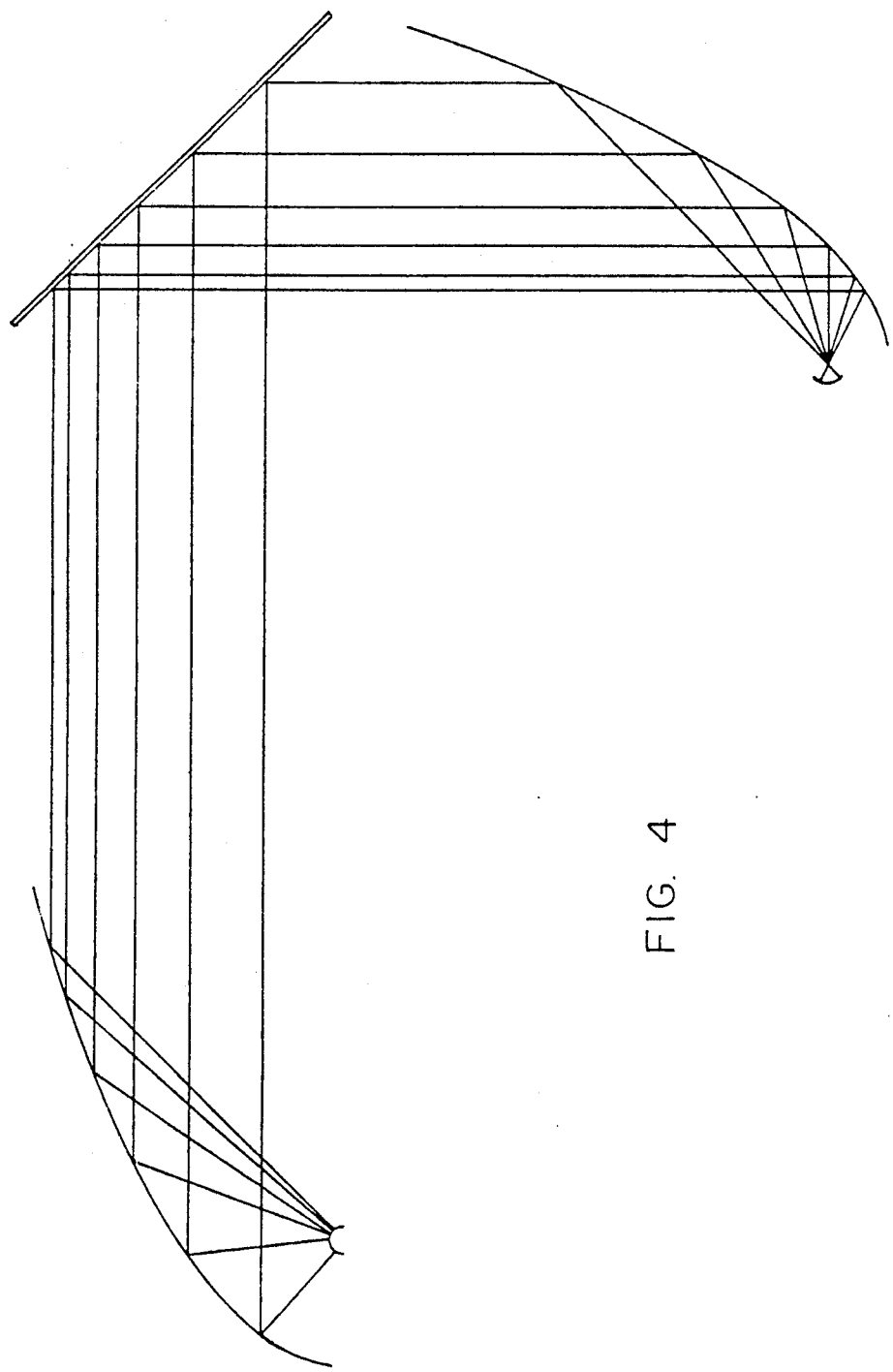
FIG. 4 is a schematic illustration of optical path differences for the optical train of the invention.

The preservation of phase is quite good in the present optical system. At the edge of the cornea where the deviation from a sphere is the most severe, the optical path difference varies by only 0.0018 mm. This would result in an error 0.0008 mm in the topography of the cornea. In addition, it is expected that this precision can be further improved by additional optimization of the optical system. FIGS. 3 and 4 illustrate the ray geometry for the calculation of data in TABLES 1 and 2, respectively.

TABLE 1

OPTICAL PATH DIFFERENCE BETWEEN THE CORNEA AND A REFERENCE SPHERE WITH THE SAME VERTEX RADIUS OF CURVATURE (mm)

| RAY | Y HEIGHT | OPLY | OPD |
|---|---|---|---|
| 1.0000 | −0.0000 | −0.0000 | 0.0000 |
| 2.0000 | 1.2000 | −0.0002 | 0.0002 |
| 3.0000 | 2.4000 | −0.0036 | 0.0036 |
| 4.0000 | 3.6000 | −0.0194 | 0.0194 |
| 5.0000 | 4.8000 | −0.0663 | 0.0663 |
| 6.0000 | 6.0000 | −0.1828 | 0.1828 |

TABLE 2

OPTICAL PATH DIFFERENCES IN THE ENTIRE OPTICAL SYSTEM (mm)

| RAY | Y HEIGHT | OPLY | OPD |
|---|---|---|---|
| 1.0000 | −0.0000 | 810.0000 | 0.0000 |
| 2.0000 | 1.2000 | 809.9998 | −0.0002 |
| 3.0000 | 2.4000 | 809.9964 | −0.0036 |
| 4.0000 | 3.6000 | 809.9811 | −0.0189 |
| 5.0000 | 4.8000 | 809.9349 | −0.0651 |
| 6.0000 | 6.0000 | 809.8190 | −0.1810 |

The principles and techniques described herein may be applicable to a more general class of optical testing problems, particularly, the testing of aspheric surfaces.

Presently the degree of asphericity which can be measured by most existing interferometric instruments is limited by detector resolution and/or operating wavelength. As the surfaces become more steeply sloped, the fringe density can exceed the resolution limits of the detector and the information is either lost or ambiguous. At the price of reduced sensitivity, two wavelength interferometry allows more aspheric or steeply sloped surfaces to be measured than would otherwise be possible. When the long equivalent wavelength interferometric information is used to remove the 2 $\pi$ ambiguities associated with shorter wavelength interferograms, one gains the facility of measuring strongly aspheric surfaces with high topographic sensitivity.

It will now be understood, that what has been disclosed herein comprises, a unique multi-wavelength interferometer utilizing a plurality of parabolic reflective surfaces to properly preserve the fidelity of light wavefronts irrespective of their wavelengths as they pass through the instrument.

In the present invention, this multi-wavelength interferometer is used to provide a long equivalent wavelength interferogram to overcome the densely-packed fringe problem of prior art interferometers. A preferred embodiment of the invention utilizes an optical train which comprises three off-axis parabolas arranged in conjunction with a beam-splitter and a reference mirror to form a Twyman-Green interferometer. The first such parabolic reflecting surface acts as a collimator. The second forms an F-number equal to 1.0 spherical wavefront converging on the surface being mapped and the third parabola reimages the test aspheric surface onto the detector. This novel optical train is especially advantageous for use for measuring highly aspherical surfaces such as the cornea of the human eye because it permits the use of two distinct optical frequencies simultaneously to generate two interferograms, as well as a set of beat fringes, which may be thought of as a third interferometric representation of the aspheric surface under test where the effective wavelength or contour interval is proportional to the inverse of the difference in the frequencies of two discrete light sources such as lasers. For this purpose, in the particular embodiment disclosed herein, an illumination subsystem is provided and comprises a pair of lasers at different preselected wavelengths in the visible spectrum. The output light of the two lasers is coaxially combined by means of a plurality of reflectors and a grating beam combiner to form a single light source at the focal point of the first parabolic reflection surface which acts as a beam collimator for the rest of the optical train. By using visible light having two distinct wavelengths, the present invention provides a long equivalent wavelength interferogram which operates at visible light wherein the effective wavelength is equal to the product of the wavelengths of the two laser sources divided by their difference in wavelength. This corresponds to an effective frequency which is equal to the difference in the frequency of the two laser sources. Consequently, the apparent or effective frequency of the combined laser light may be selected to be significantly lower than the actual frequency of the visible light of each such laser. As a result, the invention provides the advantages of what amounts to a long wavelength interferometry but without incurring the disadvantage of the negligible reflection coefficient of the human eye to long wavelength frequencies which would otherwise defeat any attempt to form an interferogram at that low frequency using only one light source. The unique fidelity preservation characteristics of the optical train of the present invention permits interferometry applications for the measurement of virtually any aspheric surface and at virtually any wavelength. Thus, while the present invention has been shown in a preferred embodiment for use in measuring or mapping the contour of the human cornea, the optical train portion thereof, would also be suitable in other interferometric applications which may be accomplished at one or more wavelengths of light.

Those having skill in the art to which the present invention pertains, will as a result of the applicant's teaching herein, now perceive various modifications which may be made to the invention. By way of example, while specific light wavelengths and parabolic reflective surface characteristics have been disclosed herein, it will be understood that the invention may be readily modified to accommodate other parabolic reflecting surface characteristics and may be used in the measurement of surface geometries at virtually any frequency including frequencies not limited to the visible portion of the spectrum. Accordingly, all such modifications and additions are deemed to be within the scope of the invention which is to be limited only by the claims appended hereto.

We claim:

1. An interferometer for providing data regarding the contour of aspheric surfaces; the interferometer comprising:
   a first off-axis parabolic reflective surface having a focal point;
   a source of light positioned at said focal point of said first parabolic reflective surface;
   a second off-axis parabolic reflective surface positioned for receiving collimated light from said first parabolic reflective, for directing said light onto one of said aspheric surfaces and for receiving light reflected from said one of said aspheric surfaces and directing said reflected light toward said first parabolic reflective surface;
   a beamsplitter positioned between said first and second parabolic reflective surfaces for re-directing a selected portion of light traveling therebetween in a direction substantially perpendicular thereto;
   a plano reference mirror positioned in spaced-apart relation to said beamsplitter along said perpendicular direction for reflecting said re-directed portion of light as a reference through said beamsplitter along said perpendicular direction;
   a third off-axis parabolic reflective surface positioned in spaced-apart relation to said beamsplitter along said perpendicular direction and opposite of said mirror for receiving said mirror-reflected light from said beamsplitter;
   said beamsplitter also redirecting said light reflected from said aspheric surface onto said third parabolic reflective surface for producing an interference fringe pattern representing the differences between said aspheric surface and a spherical reference surface.

2. The interferometer defined in claim 1 further comprising a detector; said detector being positioned relative to said third parabolic reflective surface for directing said interferometer fringe pattern onto said detector.

3. The interferometer defined in claim 1 further comprising a beamsplitter compensator plate positioned between said beamsplitter and said second parabolic reflective surface for equalizing beamsplitter-induced differences in path characteristics between said mirror-reflected light and said aspheric surface-reflect light.

4. The interferometer recited in claim 1 wherein the F-numbers of said second and third parabolic reflective surfaces are equal.

5. The interferometer recited in claim 1 wherein the F-numbers of said first, second and third parabolic reflective surfaces are each in the range of 0.6 to 20.0.

6. The interferometer recited in claim 1 wherein said source of light comprises at least one laser.

7. The interferometer recited in claim 1 wherein said source of light is a plurality of coaxial light beams, each such light beam being generated by a laser.

8. The interferometer recited in claim 1 wherein each of said light beams has a wavelength that is different from the other of said light beams.

9. The interferometer recited in claim 1 wherein said aspheric surface is a human cornea.

10. An interferometer of the type employing interference patterns between test and reference wavefronts for mapping the contour of a human cornea; said interferometer comprising:

a light source generating light simultaneously having two discrete wavelengths;

optical train means for receiving said light and preserving, without any substantial error, the optical path difference between said test and reference wavefronts at both of said wavelengths; and means for detecting the difference in interference patterns generated at each of said wavelengths;

said optical train means having a pair of off-axis parabolic reflecting surfaces having equal F-numbers.

* * * * *